United States Patent [19]

Tardivel

[11] 4,116,832
[45] Sep. 26, 1978

[54] METHOD AND MEANS FOR THE AUTOMATIC REGULATION OF SLUDGE EXTRACTION IN SEWAGE TREATMENT APPARATUS

[75] Inventor: Jacques Tardivel, Plaisir, France

[73] Assignee: Degremont, Rueil-Malmaison, France

[21] Appl. No.: 733,938

[22] Filed: Oct. 19, 1976

[30] Foreign Application Priority Data

Nov. 6, 1975 [FR] France .................. 75 33927

[51] Int. Cl.² ............................................ B01D 21/24
[52] U.S. Cl. ..................................... 210/83; 210/96 R
[58] Field of Search .......................... 210/96 R, 83 S

[56] References Cited

U.S. PATENT DOCUMENTS

| | | | |
|---|---|---|---|
| 1,957,898 | 5/1934 | Mitchell | 210/96 R |
| 3,280,975 | 10/1966 | Evans | 210/96 X |
| 3,618,766 | 11/1971 | Morey | 210/96 R |
| 3,878,094 | 4/1975 | Conley et al. | 210/96 R |
| 3,979,290 | 9/1976 | Lofflet | 210/96 R |

*Primary Examiner*—John Adee
*Attorney, Agent, or Firm*—Wenderoth, Lind & Ponack

[57] ABSTRACT

Two samples of water are taken at two predetermined levels from a variable turbidity region disposed just below the sludge bed of a sewage treatment apparatus. The samples are alternately fed to a constant-level vessel whereat the turbidity variation between the samples is measured. The rate and duration of the sludge extraction operation are controlled as a function of such turbidity variation.

9 Claims, 1 Drawing Figure

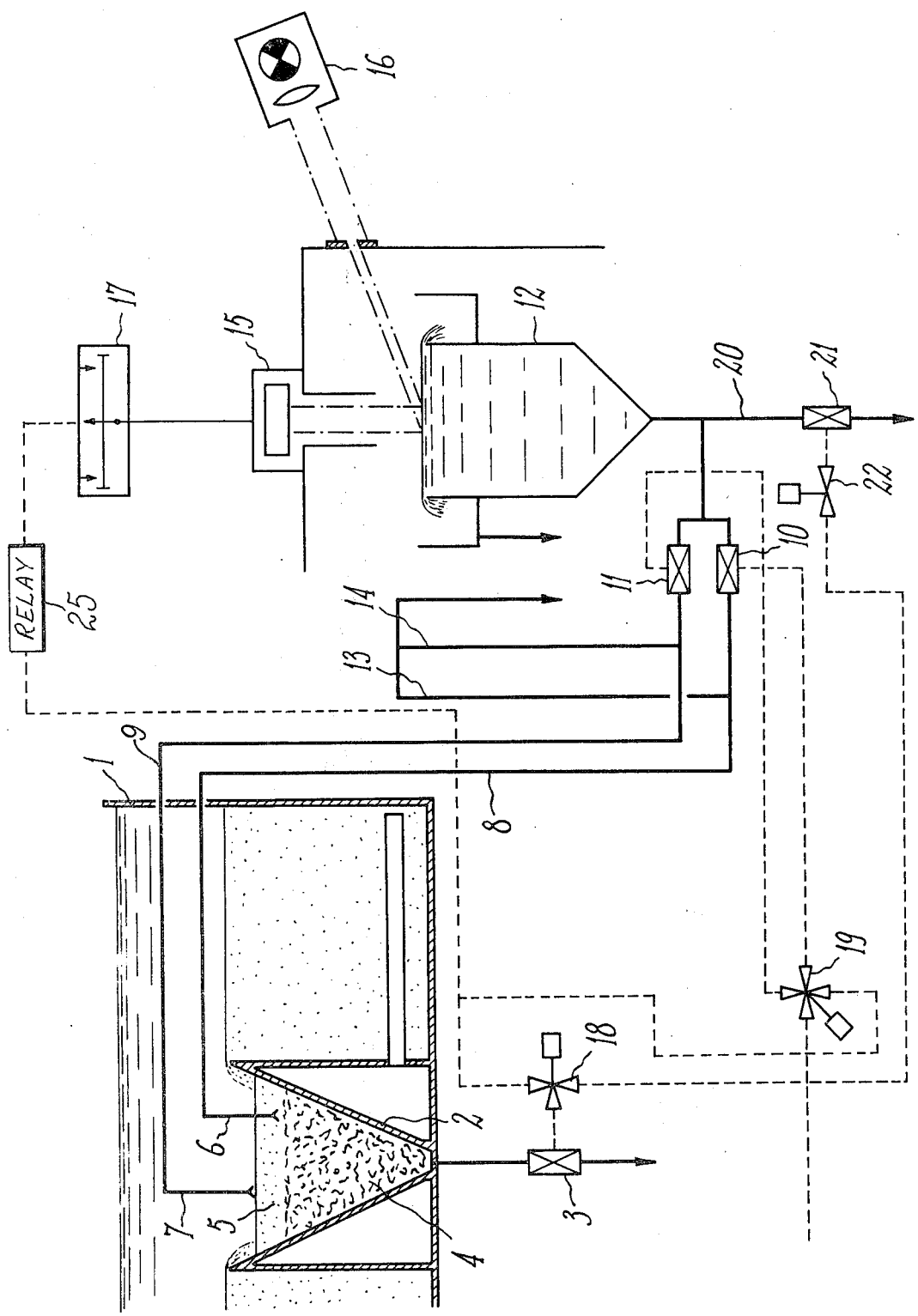

METHOD AND MEANS FOR THE AUTOMATIC REGULATION OF SLUDGE EXTRACTION IN SEWAGE TREATMENT APPARATUS

BACKGROUND OF THE INVENTION

This invention relates to a method of and means for automatically regulating the extraction of sludge from a waste water or sewage treatment apparatus, notably a sludge-bed type settling tank.

As a rule, sludge is concentrated in a so-called concentrator sludge pit. Sludge can be removed therefrom by using continuously-operating or intermittently-operating devices. It is known to adjust the rate and duration of these sludge extractions or purifying steps, by using means responsive to the input of sewage or waste water introduced into the apparatus and or to a preset sludge extraction rate. The sludge accumulation is not at all times exactly proportional to the throughput of water to be treated, for it also depends on the specific nature of this water, i.e. the nature of the sludge. Therefore, the sludge level in the concentrator must be checked continuously. This level is usually controlled by means of a densimeter or a capacitive or ultrasonic probe. In addition, it is known that above the sludge level there is a region in which the water muddiness is more or less preserved, as a function of the specific nature of the suspended solids therein, hence of the sludge type. Therefore, it is extremely difficult to determine the precise upper level of the sludge. Using a densimeter or hydrometer requires frequent adjustments. Besides, the results obtained by using probes are inaccurate, since probes do not take into account this region of diffused cloudiness or turbidity which varies with sudden changes in the waste water input supplied to the apparatus. As a consequence of these delicate and necessarily inaccurate measurements of the sludge level, the extraction rate and duration are such that, since they do not take into account the level variations, either an excessive extraction with attendant loss of water and costly reagents, or an insufficient extraction with sludge overflow and an increase in the turbidity of the treated water, are observed.

SUMMARY OF THE INVENTION

It is the primary object of this invention to detect with precision the sludge level and regulate the sludge extraction operation as a function of the sludge level with due consideration for turbidity variation likely to occur in the region located just above the sludge, in order to avoid any loss of water and also to prevent any suspended solids from being carried away by the treated water.

This object is achieved according to the present invention, by providing a method including taking from the variable-turbidity region located just above the sludge bed samples at two different predetermined levels. The samples are alternately fed to a constant-level vessel whereat the turbidity variation between these two samples is measured. Finally, the sludge extraction rate and duration is controlled as a function of this turbidity variation.

BRIEF DESCRIPTION OF THE DRAWING

Other objects, features and advantages of the present invention will be apparent from the following detailed description, taken with the accompanying drawing, wherein:

The single FIGURE is a schematic view of a preferred embodiment of the present invention.

DETAILED DESCRIPTION OF THE INVENTION

It is to be understood that the following description refers to a specific embodiment of the invention, given by way of illustration only, and not of limitation, since many other arrangements may be employed without departing from the scope of the invention, as will readily occur to those conversant with the art.

In the settling tank 1 the sludge accumulates in the concentrator 2 from which it is intermittently extracted by means of a conduit equipped with a diaphragm valve or butterfly valve 3. Overlying the sludge bed 4 is a liquid region 5 the turbidity of which is dependent at any given time to the input of waste water entering the settling tank and also to the specific nature of the water to be treated.

In this variable turbidity region 5 and according to a specific feature of this invention, two samples of the liquid are taken at two predetermined levels, the uppermost level being consistent with the desired extraction rate. The samples are taken by means of a pair of test-tubes 6 and 7 provided with inverted funnels at their ends in order to avoid any concentration variations within the samples. These samples are passed alternately in succession by means of pipe lines 8 and 9 provided with control valves 10 and 11 to a constant-level vessel or tank 12.

Advantageously, the valves 10 and 11 are of the direct-passage diaphragm type. The pipe lines 8 and 9 are each provided with overflow devices, consisting for example of stirrup-shaped pipes 13 and 14 having their upper lever disposed slightly above the liquid level in the constant-level vessel 12. Thus, the provision of these overflow devices will prevent solid matters from accumulating in the pipe system and also will prevent any idle period in the measurement upon opening the valves 10 and 11.

The variations in the turbidity of the samples taken from the constant level vessel are detected by a photo-resistant cell 15 responsive to the more or less pronounced intensity of the light beam emitted from a light source 16, for instance an electric bulb, this light beam being adsorbed by the surface of the waste water contained in vessel 12 and refracted in a fixed angular direction. The turbidity variation recorded by the photoresistant cell is transmitted to a galvanometer 17 having adjustable contacts.

Maximum and minimum turbidity values M and $m$, respectively, are selected beforehand. When the maximum turbidity value M displayed by the galvanometer 17 is attained, a relay system 25 enables a solenoid valve 18 to control the opening of valve 3, to extract sludge 4 from concentrator 2, through the medium of a power fluid, e.g. air or water. At the same time, the relay system 25 enables another solenoid valve 19 to control the closing of one diaphragm valve 11 while opening the other diaphragm valve 10. The sample continues to be taken at lower test tube 6 due to the provision of the overflow device 13, and this sample passes through open valve 10 to vessel 12.

The sludge extraction operation is continued until the sludge level in concentrator 2 reaches the lower sample pick-up means or test tube 6. The turbidity thus gradually decreases in the constant-level vessel 12. When the minimum turbidity value $m$ is displayed or read by the galvanometer 17, the solenoid valve 18 controls the valve 3 to stop the sludge extraction operation, and at the same time the solenoid valve 19 opens valve 11 and closes valve 10. The sample is still picked up at the upper test tube 7 due to the provision of the overflow device 14, and this sample is now passed through open valve 11 to vessel 12.

The constant level vessel 12 includes a draining device 20 for removing heavier particles which settle in the bottom thereof. This draining device comprises a pipe provided with a diaphragm valve 21 controlled by a solenoid valve 22.

With this arrangement, the degree or precision and regularity of the rate and time or duration of the sludge extraction operation are such that the efficiency of the waste water treatment is greatly improved. Sludge concentrates more regularly and its concentration is more pronounced. Thus, given the same sludge-bed depth, a 8 gram/liter concentration of suspended solids has been obtained, compared with 1 to 1.5 g/l measured in conventional systems. The loss of water is very low, and the necessary amount of secondary treatment may be reduced.

EXAMPLE

From a settling apparatus sludge was extracted according to the conventional method, on the one hand, and by using the method of this invention, on the other hand.

The sewage contained 15 to 25 mg/l of suspended solids with a turbidity of 7 to 9 UI. This water was treated with 70 g/m$^3$ of alumina sulfate, 2.4 g/m$^3$ of SiO$_2$ and 15 g/m$^3$ of activated carbon in powder form. Therefore, a sludge bed consisting essentially of alumina hydroxid having a cohesion coefficient of 1.2 to 1.5 was available.

The raw water output was 900 m$^3$/h.

By applying the conventional method, sludge had to be removed every 2 minutes, and each removal operation took 50 seconds. The sludge concentration was extremely moderate, and the turbidity of a sample taken at a depth of 35 cm below the overflow level in the concentrator ranged from 3 to 5 UI. By applying the method of this invention, much more concentrated sludge (55 UI) than before was extracted under the same conditions, the extraction taking place automatically every 90 minutes only, and each removal operation took 3 mn and 30 seconds. Moreover, in comparison with the waste water input introduced into the apparatus, only 0.5% of the sludge was extracted by operating according to this invention, whereas the conventional procedure involved a 11.7% sludge extraction.

The results are shown in the following Table:

| Mode of operation | Waste water output m3/h | Extraction rates and durations | | Suspended solids extracted | | Sludge turbidity | Sludge extract % |
| --- | --- | --- | --- | --- | --- | --- | --- |
| | | Time intervals | Duration | Start | End | | |
| Conventional method | 900 | 2mn | 50 s. | 1.3 | .92 | 3 to 5 UI | 11.7 |
| Method of present invention | 900 | 90 mn | 3mn and 30 sec. | 8.05 | 7 | 55 UI | 0.5 |

On the other hand, with variations in the waste water input (this input dropping suddenly from 1,200 m$^3$/h to 450 m$^3$/h), a consolidation of the sludge bed was observed and the overflow level resumed its normal condition after only 3 to 4 hours. During this time, the device of this invention does not control any sludge extraction, in contrast with the conventional method in which the sludge extraction takes place continuously.

What is claimed as new is:

1. A process for automatically extracting accumulated sludge from a sludge concentrator employed in a sludge-bed sewage treatment system, wherein said concentrator has in a lower portion thereof accumulated sludge and above said sludge a liquid region of vertically variable turbidity, the turbidity of said region gradually increasing as said sludge accumulates in said concentrator, and said turbidity of said region gradually decreasing as sludge is extracted from said concentrator, said process comprising:

continually taking a first sample of the liquid in said region at a first vertical level therein;

continuously taking a second sample of the liquid in said region at a second vertical level therein, said level being higher than said first level;

alternately passing one of said first and second liquid samples to a vessel positioned separately from said concentrator, while passing the other of said first and second liquid samples to an overflow;

continuously measuring the turbidity of the liquid in said vessel, to thereby continuously obtain a measurement of the turbidity of said region; and controlling, as a function of said turbidity measurement, extraction of accumulated sludge from said concentrator and which of said first and second samples is passed to said vessel, such that when said turbidity measurement reaches a determined maximum value sludge is extracted from said concentrator and said first sample is passed to said vessel, whereafter said turbidity measurement will decrease, and such that when said turbidity measurement reaches a determined minimum value extraction of said sludge is stopped and said second sample is passed to said vessel, whereafter said turbidity measurement will increase.

2. A process as claimed in claim 1, wherein said step of measuring the turbidity of the liquid in said vessel comprises directing a beam of light toward the upper surface of said liquid in said vessel, whereby said beam of light is refracted, and measuring the intensity of the thus refracted light as a function of turbidity of said liquid.

3. An apparatus for automatically extracting accumulated sludge from a sludge concentrator employed in a sludge-bed sewage treatment system, wherein said concentrator has in a lower portion thereof accumulated sludge and above said sludge a liquid region of vertically variable turbidity, the turbidity of said region gradually increasing as said sludge accumulates in said concentrator, and said turbidity of said region gradually decreasing as sludge is extracted from said concentrator, said apparatus comprising:

first means for continuously taking a first sample of the liquid in said region at a first vertical level therein;

second means for continuously taking a second sample of the liquid in said region at a second vertical level therein, said second level being higher than said first level;

a vessel positioned separately from said concentrator;

means for alternately passing one of said first and second liquids samples to said vessel while passing the other of said first and second liquid samples to an overflow;

means for continuously measuring the turbidity of the liquid in said vessel, and for thereby obtaining a continuous measurement of the turbidity of said region;

means associated with said concentrator for extracting sludge therefrom; and control means, operable by said measuring means and connected to said sludge extracting means and to said passing means, for operating said sludge extraction means to extract sludge from said concentrator and for operating said passing means to pass said first sample to said vessel upon said measuring means measuring a determined maximum turbidity value, whereafter said turbidity value will decrease, and for operating said sludge extraction means to stop extraction of sludge from said concentrator and for operating said passing means to pass said second sample to said vessel upon said measuring means measuring a determined minimum turbidity value, whereafter said turbidity value will increase.

4. An apparatus as claimed in claim 3, wherein said passing means comprises a first pipe line connected to said first sample taking means and said vessel, a first valve in said first pipe line, a first overflow pipe joining said first pipe line at a position between said first sample taking means and said first valve, a second pipe line connected to said second sample taking means and said vessel, a second valve in said second pipe line, and a second overflow pipe joining said second pipe line at a position between said second sample taking means and said second valve.

5. An apparatus as claimed in claim 4, wherein said measuring means comprises a light source for directing a beam of light toward the upper surface of said liquid in said vessel, whereby said beam of light is refracted, and means for measuring the intensity of the thus refracted light as a function of the turbidity of said liquid.

6. An apparatus as claimed in claim 5, wherein said control means comprises a galvanometer connected to said intensity measuring means, and a relay system operable by said galvanometer and connected to said first and second valves and to said sludge extraction means.

7. An apparatus as claimed in claim 3, wherein said measuring means comprises a light source for directing a beam of light toward the upper surface of said liquid in said vessel, whereby said beam of light is refracted, and means for measuring the intensity of the thus refracted light as a function of the turbidity of said liquid.

8. An apparatus as claimed in claim 7, wherein said control means comprises a galvanometer connected to said intensity measuring means, and a relay system operable by said galvanometer and connected to said passing means and to said sludge extraction means.

9. An apparatus as claimed in claim 3, wherein each of said first and second sample taking means comprises a vertically extending pipe-shaped member having at the lower end thereof an outwardly and downwardly flared funnel.

* * * * *